(12) United States Patent
Sakamoto

(10) Patent No.: US 8,236,291 B2
(45) Date of Patent: Aug. 7, 2012

(54) ANTIBACTERIAL AND DEODORANT FIBER, FIBER FORMED ARTICLE, AND FIBER PRODUCT

(75) Inventor: Kazuyuki Sakamoto, Osaka (JP)

(73) Assignees: ES Fiber Visions Co., Ltd., Osaka (JP); ES Fiber Visions Hong Kong Limited, Kowloon (HK); ES Fiber Visions LP, Athens, GA (US); ES Fiber Visions APS, Verde (DK)

( * ) Notice: Subject to any disclaimer, the term of this patent is extended or adjusted under 35 U.S.C. 154(b) by 375 days.

(21) Appl. No.: 12/532,511

(22) PCT Filed: Apr. 4, 2008

(86) PCT No.: PCT/JP2008/057121
§ 371 (c)(1),
(2), (4) Date: Sep. 22, 2009

(87) PCT Pub. No.: WO2008/123631
PCT Pub. Date: Oct. 16, 2008

(65) Prior Publication Data
US 2010/0086511 A1    Apr. 8, 2010

(30) Foreign Application Priority Data

Apr. 4, 2007   (JP) .................................. 2007-98669

(51) Int. Cl.
*A61L 9/00* (2006.01)
*A61L 9/01* (2006.01)
(52) U.S. Cl. ..................................... 424/76.1
(58) Field of Classification Search .................. 424/76.1
See application file for complete search history.

(56) References Cited

U.S. PATENT DOCUMENTS

2005/0255078 A1   11/2005   Sakamoto et al.

FOREIGN PATENT DOCUMENTS

| | | |
|---|---|---|
| CN | 1584184 | 2/2005 |
| JP | 62-191571 | 8/1987 |
| JP | 4-45824 | 2/1992 |
| JP | 5-156510 | 6/1993 |
| JP | 06-228823 | 8/1994 |
| JP | 8-296173 | 11/1996 |
| JP | 9-131393 | 5/1997 |
| JP | 2000-110068 | 4/2000 |
| JP | 2000-160478 | 6/2000 |
| JP | 2000-303250 | 10/2000 |
| JP | 2001-527165 | 12/2001 |
| JP | 2002-128680 | 5/2002 |
| JP | 2002-212877 | 7/2002 |
| JP | 2003-253559 | 9/2003 |
| JP | 2004-176225 | 6/2004 |
| JP | 2004-187790 | 7/2004 |
| JP | 2005-299036 | 10/2005 |
| JP | 2005-330641 | 12/2005 |
| JP | 2006-249559 | 9/2006 |
| JP | 2007-107144 | 4/2007 |
| WO | 99/32706 | 7/1999 |

*Primary Examiner* — David J Blanchard
*Assistant Examiner* — Trevor Love
(74) *Attorney, Agent, or Firm* — Hamre, Schumann, Mueller & Larson, P.C.

(57) ABSTRACT

There is provided an antibacterial and deodorant fiber that exhibits excellent inhibition of bacterial growth, is capable of responding to a wide variety of odorants, does not discolor easily, and can maintain stable performance. An antibacterial and deodorant fiber characterized in that a fiber treatment agent comprising at least a component (A), and a component (B) and/or a component (C) below are attached thereto at 0.2 to 5 wt % of the total weight of the fiber, the fiber treatment agent containing 20 to 80 wt % of the component (A), and 80 to 20 wt % of the component (B) and/or the component (C):

(A) at least one plant extract, said plant being at least one selected from the group consisting of tea leaves, aloe, bamboo, bamboo grass, Japanese butterbur (*Petasites japonica*), loofa (*Luffa cylindrica*), horsetail (*Equisetum arvense*), Japanese mugwort (*Artemisia princeps*), geranium (*Geranium nepalense* var. thunbergii), persimmon, and grapefruit;

(B) at least one nonionic surfactant selected from the group consisting of an alkylene oxide adduct type nonionic surfactant and a polyhydric alcohol type nonionic surfactant;

(C) at least one anionic surfactant selected from the group consisting of a carboxylic acid salt, sulfonic acid salt, sulfuric acid ester salt, and phosphoric acid ester salt.

10 Claims, No Drawings

ANTIBACTERIAL AND DEODORANT FIBER, FIBER FORMED ARTICLE, AND FIBER PRODUCT

TECHNICAL FIELD

The present invention relates to an antibacterial and deodorant fiber, and more particularly to an antibacterial and deodorant fiber suitable for use in absorbent articles such as diapers, napkins, pads or the like, medical hygiene supplies, daily living-related materials, general medical supplies, bedding materials, filter materials, nursing care products, and pet products, or the like, and to a process for producing the same, and to a fiber formed article and a fiber product using the same.

BACKGROUND ART

Due to recent changes in lifestyle, an increasing densification and air-tightness in residential environments, and the like, various bacteria and molds are becoming more widespread in human living spaces. Especially in an environment with high temperature and humidity like Japan, bacteria and molds proliferate easily on the surfaces of textile materials such as absorbent articles and other hygiene supplies, clothing, and the like. This can result in skin disorder, a loss of product quality due to fiber deterioration and discoloration, or an unpleasant odor that accompanies the proliferation of microbes. In particular, the development of an unpleasant odor is considered to be a problem, and demand has grown in recent years for both bacterial growth inhibition and unpleasant odor clearance. Typical odor-causing components include ammonia, trimethylamine and other basic gases; sulfur-containing compounds such as hydrogen sulfide, and methyl mercaptans; and short chain fatty acids such as acetic acid, butyric acid, valeric acid and caproic acid, produced by bacterial decomposition of secretions from the sweat glands, sebaceous glands, etc. Additionally, nitrogen-containing cyclic compounds such as indoles, skatoles, and the like are known as ingredients that can make people feel uncomfortable.

Typical methods for removing these odor-causing substances include physical adsorption methods wherein the odor is adsorbed by using a porous medium such as activated charcoal, silica gel, and the like; chemical methods wherein the odor-causing substance is reacted in a neutralizing or oxidation reaction and removed; and sensory methods wherein the uncomfortable feeling is suppressed by a strong fragrance, and the like.

On the other hand, the unpleasant odor accompanying the proliferation of microbes can be controlled indirectly by imparting antibacterial properties to fibers. Unpleasant odors can be efficiently removed and the generation thereof is controlled by using a combination of the odor-removing methods noted above. In addition to conventional means of adding an inorganic antibacterial and deodorizing agent containing silver, zinc, and the like to the fibers, for example, Japanese Patent Application Publication (hereunder referred to as "JP KOKAI") No. 2000-303250 has proposed fibers with catechins, which are contained in a tea leaf extract and the like, added thereto, JP KOKAI No. 2003-253559 has proposed fibers with rosemary essential oil and the like added thereto.

Although antibacterial and deodorant fibers to which the aforementioned tea leaf extract and plant liquid extract are added have good antibacterial and deodorant properties, problems remain because these additives are easily oxidized by oxidants in the air such as nitrogen dioxide and other nitrogen compounds, resulting in discoloration including yellowing, reddening, and the like. Consequently, the antibacterial and deodorant properties are not only decreased thereby, but the use of such fibers in paper diapers, sanitary napkins, incontinence pads and other hygiene products has also been limited, mainly due to concerns about unacceptable appearance caused by discoloration.

DISCLOSURE OF THE INVENTION

An object of the present invention is to provide an antibacterial and deodorant fiber that has an excellent growth inhibitory effect on bacteria, is capable of countering a variety of odor-producing substances, is not easily discolored, and is capable of maintaining stable performance. A further object of the present invention is to provide a process for producing such an antibacterial and deodorant fiber. Additionally, a further object of the present invention is to provide a fiber formed article using the above antibacterial and deodorant fiber, and to provide a fiber product using the above fiber formed article.

After diligent study to solve the aforementioned problems, the inventors discovered that a fiber having the composition described below exhibited bacterial growth inhibition and deodorant performance, did not discolor easily, and maintained its antibacterial and deodorant properties over a long period of time, thus completing the present invention.

Therefore, the present invention is an antibacterial and deodorant fiber characterized in that a fiber treatment agent comprising at least a component (A), and a component (B) and/or a component (C) described below is attached thereto at 0.2 to 5 wt % of the total weight of the fiber, the fiber treatment agent containing 20 to 80 wt % of the component (A), and 80 to 20 wt % of the component (B) and/or the component (C):

(A) at least one plant extract, said plant being at least one selected from the group consisting of tea leaves, aloe, bamboo, bamboo grass, Japanese butterbur (*Petasites japonica*), loofa (*Luffa cylindrica*), horsetail (*Equisetum arvense*), Japanese mugwort (*Artemisia princeps*), geranium (*Geranium nepalense* var. thunbergii), persimmon, and grapefruit;

(B) at least one nonionic surfactant selected from the group consisting of an alkylene oxide adduct type nonionic surfactant and a polyhydric alcohol type nonionic surfactant;

(C) at least one anionic surfactant selected from the group consisting of a carboxylic acid salt, sulfonic acid salt, sulfuric acid ester salt, and phosphoric acid ester salt.

A preferred embodiment of the present invention includes an antibacterial and deodorant fiber characterized in that the polyphenols contained in the above plant extract are 1 to 20 wt % with respect to the weight of the above fiber treatment agent; and an antibacterial and deodorant fiber wherein the attached amount of the component (A) above is at least 0.1 wt % with respect to the total weight of the fiber.

Specifically, the alkylene oxide adduct nonionic surfactant of the component (B) above is selected from the group consisting of a polyoxyalkylene alkyl ether, a polyoxyalkylene alkyl phenol, a polyoxyalkylene higher fatty acid ester, a polyoxyalkylene polyhydric alcohol higher fatty acid ester, a polyoxyalkylene higher aliphatic amine, a polyoxyalkylene higher fatty acid amide, and a polyoxyalkylene alkyl alkanol amide. Additionally, the polyhydric alcohol nonionic surfactant of the component (B) is specifically selected from the group consisting of a higher fatty acid ester of glycerin, pentaerythritol, sorbitan or sorbitol; a sucrose fatty acid ester; and a higher fatty acid alkanol amide.

The antibacterial and deodorant fiber of the present invention contains therein zinc oxide and/or the complex oxide represented by General Formula (1) below in the range of 0.1 to 10 wt % with respect to the total weight of the fiber:

$$M^{2+}_{(1-x_1)} M^{3+}_{x_1-\delta} O \tag{1}$$

(wherein $M^{2+}$ represents zinc or a divalent metal having zinc as an essential component thereof, $M^{3+}$ represents a trivalent metal selected from Al, Fe, and Ce; $x_1$ represents a number in the range $0 < x_1 \leq 0.5$; and $\delta$ represents a cation lattice defect).

A preferred embodiment of the antibacterial and deodorant fiber of the present invention comprises a conjugate fiber containing at least two types of thermoplastic resin, and additionally comprises a sheath-core type conjugate fiber, at least one type of the thermoplastic resin being a polyolefin resin, and the resin being located in the sheath member thereof.

A preferred embodiment of the antibacterial and deodorant fiber of the present invention comprises a conjugate fiber, and characterized in that the above metal oxide is kneaded and mixed into the sheath member of the conjugate fiber.

The present invention is intended for a fiber formed article using the above antibacterial and deodorant fiber, and for a fiber product using that fiber formed article.

The present invention also includes a process for producing the antibacterial and deodorant fiber, characterized in that a fiber treatment agent containing at least a component (A), and a component (B) and/or a component (C) below is attached to the fiber at 0.2 to 5 wt % based on the total weight of the fiber; the component (A) comprises 20 to 80 wt % and the component (B) and/or the component (C) comprises 80 to 20 wt % of the fiber treatment agent; and the component (A), and the component (B) and/or the component (C) are applied to the fiber simultaneously, or component the (B) and/or the component (C) is applied to the fiber after the component (A) is applied thereto, or the component (A) is applied to the fiber after the component (B) and/or the component (C) is applied thereto:

(A) at least one plant extract, said plant being at least one selected from the group consisting of tea leaves, aloe, bamboo, bamboo grass, Japanese butterbur (*Petasites japonica*), loofa (*Luffa cylindrica*), horsetail (*Equisetum arvense*), Japanese mugwort (*Artemisia princeps*), geranium (*Geranium nepalense* var. thunbergii), persimmon, and grapefruit;

(B) at least one nonionic surfactant selected from the group consisting of an alkylene oxide adduct type nonionic surfactant and a polyhydric alcohol type nonionic surfactant;

(C) at least one anionic surfactant selected from the group consisting of a carboxylic acid salt, sulfonic acid salt, sulfuric acid ester salt, and phosphoric acid ester salt.

The antibacterial and deodorant fiber of the present invention exhibits excellent bacterial growth inhibition and excellent deodorant performance by adding thereto at least one kind of plant extract selected from a group consisting of tea leaves, aloe, bamboo, bamboo grass, Japanese butterbur (*Petasites japonica*), loofa (*Luffa cylindrica*), horsetail (*Equisetum arvense*), Japanese mugwort (*Artemisia princeps*), geranium (*Geranium nepalense* var. thunbergii), persimmon, and grapefruit. In addition, discoloration of the fiber can be inhibited, excellent appearance can be maintained, and the antibacterial and deodorant performance can be realized over a long period of time by including therein the designated nonionic surfactant and/or anionic surfactant.

Because the fiber formed article obtained from the antibacterial and deodorant fiber of the present invention has excellent antibacterial properties and deodorant performance, the excellent antibacterial properties and deodorant performance can be utilized in a variety of ways, e.g., absorbent articles such as diapers, napkins, incontinence pads, etc.; medical hygiene supplies such as gowns, scrubs, etc.; interior furnishing materials such as wall coverings, Japanese translucent sliding window paper, floor coverings, etc.; daily living-related materials such as various covering cloths, garbage container coverings, etc.; toilet related products such as disposable toilets, toilet seat covers, etc.; pet products such as pet sheets, pet diapers, pet towels, etc.; general medical supplies; bedding materials; filter materials; nursing care products, and so forth.

BEST MODE FOR CARRYING OUT THE INVENTION

The present invention is explained below in detail.

The antibacterial and deodorant fiber of the present invention is a fiber wherein a fiber treatment agent comprising at least a component (A), and a component (B) and/or a component (C) described below is attached thereto at 0.2 to 5 wt % of the total weight of the fiber, and the ratio of the aforementioned components in the fiber treatment agent is a range of 20 to 80 wt % of component (A), and 80 to 20 wt % of component (B) and/or component (C).

Component (A) is at least one plant extract, said plant being at least one selected from the group consisting of tea leaves, aloe, bamboo, bamboo grass, Japanese butterbur (*Petasites japonica*), loofa (*Luffa cylindrica*), horsetail (*Equisetum arvense*), Japanese mugwort (*Artemisia princeps*), geranium (*Geranium nepalense* var. thunbergii), persimmon, and grapefruit; component (B) is at least one nonionic surfactant selected from the group consisting of an alkylene oxide adduct type nonionic surfactant and a polyhydric alcohol type nonionic surfactant; and component (C) is at least one anionic surfactant selected from the group consisting of a carboxylic acid salt, sulfonic acid salt, sulfuric acid ester salt, and phosphoric acid ester salt.

The plant used in component (A) of the present invention is at least one of plant selected from the group consisting of tea leaves, aloe, bamboo, bamboo grass, Japanese butterbur (*Petasites japonica*), loofa (*Luffa cylindrica*), horsetail (*Equisetum arvense*), Japanese mugwort (*Artemisia princeps*), geranium (*Geranium nepalense* var. thunbergii), persimmon, and grapefruit. Preferably extracts of 2 or more types of plants are used to ensure that a variety of active ingredients, e.g., polyphenols, are present in the plant extract used as component (A).

The part of the plant used for making the plant extract may be an above-ground part, underground-part, fruit thereof, skin of the fruit thereof, or seeds thereof. In addition to the 1 or more types of plants, an extract of a plant such as Japanese cypress (*Chamaecyparis obtusa*), beech, Japanese cedar (*Selaginella tamariscina*), chameleon plant (*Houttuynia cordata*), orange, *Canaga odorata*, chamomile, grapefruit, sandalwood, cinnamon, jasmine, sage, geranium, tea tree, basil, peppermint, lemon, eucalyptus, lime, lavender, lemon grass, rosemary, and the like may be used therein.

Examples of methods for obtaining the plant extract include using the plant just as harvested or after drying, either shredded or unshredded, and performing extraction using 1 or a mixture of 2 or more types of solvents such as water, an aqueous solution of inorganic acid, an aqueous solution of an organic acid, an aqueous solution of an inorganic alkali, an organic solvent, and the like as the extraction solvent. A plant extract liquor is obtained by filtering the obtained liquid extract, and then enriching the same by concentration in vacuo and the like. Alternatively, the extraction solvent can be evaporated, and the extract obtained as a solid.

Either a liquid or solid plant extract may be used as a liquid plant extract when applied to the fiber, and if the original extract is a solid, it may be used by dissolution in a suitable solvent, or by dissolution in component (B) and/or component (C) and optionally a suitable solvent as desired.

An aqueous solution of hydrochloric acid, sulfuric acid, nitric acid, and the like can be listed as an example of the inorganic acid aqueous solution serving as the extraction solvent, and the preferred pH thereof is 2 to 6. An aqueous solution of acetic acid, citric acid, and the like can be listed as an example of the organic acid aqueous solution, and the preferred pH thereof is 2 to 6. An aqueous solution of sodium bicarbonate, sodium carbonate, sodium hydroxide, sodium citrate, potassium carbonate, potassium hydrogen carbonate, potassium hydroxide, and potassium citrate, and the like can be listed as an example of the inorganic alkaline aqueous solution, and the preferred pH thereof is 8 to 12. Moreover, the use of a mixed buffer solution of the above inorganic acid aqueous solution and the above alkaline aqueous solution is preferred.

In addition to alkanes such as hexane and the like, ethers, ketones, and alcohols can be listed as examples of the organic solvent. In particular, use of a lower alcohol of 1 to 3 carbon atoms, glycerin, propylene glycols, 1, 3-butylene glycol, polyethylene glycol, and/or an aqueous solution thereof is preferred.

The extraction treatment can be performed by methods such as cold extraction, warm extraction, heat-reflux, percolation, and the like. The present invention does not particularly limit the specific extraction method, and other examples include steam distillation methods wherein extraction is performed using steam, milling methods, supercritical extraction methods performed with carbon dioxide gas in a supercritical state, and the like. Such extraction methods can be referenced by examining, for example, the Examples sections of Japanese Patent Application Publication Nos. H8-296173, H9-131393, and 2006-249599.

Commercial products can be used as the plant extract of component (A), and examples of such commercial products include "L-17W" (extract of bamboo grass, Japanese butterbur, loofa, horsetail, and Japanese mugwort) manufactured by Kankyo Kagaku Kaihatsu K.K.; "SANFURABON" (tea extract) manufactured by Taiyo Kagaku Co., Ltd.; "TEAFURAN" and "TEAFURAN 30A" (tea extract, tea polyphenols 40%) manufactured by Ito En, Ltd.; "NEOBANPUSU 2000" (bamboo extract) manufactured by Shiraimatsu Pharmaceutical Co., Ltd.; "PANSHIRU" (persimmon extract, persimmon polyphenols 5%) and "DESFAN" (grapefruit extract) manufactured by Rilis Co., Ltd., and the like. The plant extract used as component (A) is not particularly limited by the present invention provided it satisfies the requirements thereof.

The active ingredient contained in the plant extract of component (A) includes a variety of ingredients such as polyphenols, including flavonoids, especially catechins, tannins, etc., terpenes, terpenoids, limonenes, and the like. Among these active ingredients, the antibacterial and deodorant properties of polyphenols are very good, but it is especially desirable that the weight ratio of polyphenols in the fiber treatment agent attached to the fibers be 1 to 20 wt % because among the active ingredients obtained from plants, polyphenols in particular are easily discolored by oxidation. When the polyphenol ratio lies within this range, the desired antibacterial and deodorant properties are realized while discoloration such as yellowing or reddening are suppressed.

Tea leaves, bamboo, bamboo grass, Japanese buttebur, loofa, horsetail, Japanese mugwort, and persimmon are preferred as the plant used in component (A), and tea leaves, bamboo, bamboo grass, Japanese buttebur, loofa, horsetail, and Japanese mugwort are especially preferred.

Examples of methods for qualitatively and quantitatively verifying the content of polyphenols in the fiber treatment agent attached to the fibers include methods utilizing a colorimetric analytical method such as the Folin-Denis method, Folin-Ciocalteu method and the like; methods utilizing an electrochemical analytical procedure based on a sensor (for example, the PA-20 polyphenol measuring instrument manufactured by Toyobo Co., Ltd.); and the like, wherein the fiber treatment agent attached to the surface of the fibers or contained therein is extracted from the fibers with a solvent comprising water or another polar solvent and/or a nonpolar solvent and the extract is analyzed.

Furthermore, various types of ingredients in addition to polyphenols such as terpenes, terpenoids, limonenes and the like noted above are contained in component (A), and it is possible to perform qualitative and quantitative analysis thereof, for example, by using reverse phase HPLC with an ODS column and the like, and using gas chromatography such as GC/MS and the like. Polyphenol analysis is also possible with these methods; therefore analysis is by no means limited to these exemplary methods, and the content of ingredients can be verified by other methods as well. Naturally, the use of these methods in combination is also preferred.

Excellent antibacterial and deodorant properties can be realized by using component (A) constituting the above active ingredients. If component (A) used in the present invention is merely attached to the surface of the fibers or contained therein, resistance to discoloration by oxidants in the atmosphere will be insufficient, and both quality and stability will be markedly diminished after the fiber, fiber formed article, or fiber product has been fabricated. Therefore, by mixing component (B) and/or component (C) with component (A) and attaching the same to the fibers, or by attaching component (A) to the fibers and then attaching component (B) and/or component (C) thereon (as a finishing coat), long term resistance to discoloration in the outside air can be realized, and it is possible to obtain better antibacterial and deodorant properties than a case wherein only component (A) has been attached to the fibers.

Conjugated compounds such as quinones and the like, nitro compounds, and other colored compounds are produced by the action of oxidants such as nitrogen oxides, ozone, and the like on plant extracts typified by polyphenols. The exact action thereof is still unknown, but one hypothesis is that in the process of the above reaction, if the pH of the fiber surface exceeds 8, the above reaction is further accelerated by the reaction and consumption of nitrous acid, etc., produced as byproducts. However, if component (B) and/or component (C) is present, discoloration is suppressed because the pH of the fiber surface is maintained in the vicinity of 4 to 8. Additionally, reaction of the plant extract with the outside air is kept at a minimum and natural loss of the plant extract due to evaporation and the like is controlled, by enveloping the plant extract.

The hydrophilicity and antistatic properties of the plant extract are not sufficiently even during fiber processing, and static charges arise in the manufacturing steps from fibers to webs and slivers because the fibers rub against the carding machine or air-laid machine, and the workability thereof tends to decline. By mixing or coating component (A) with component (B) and/or component (C), however, sufficient antistatic properties can be obtained during high speed carding conditions, and concurrently the plant extract on the fiber surface can be protected against removal. Therefore, it is possible to obtain better antibacterial and deodorant properties than a case wherein only component (A) has been attached to the fibers.

Examples of component (B) used in the present invention include an nonionic surfactant selected from alkylene oxide adduct nonionic surfactants (hereinafter, component (B1)), and polyhydric alcohol nonionic surfactants (hereinafter, component (B2)).

An alkyl of 12 to 24 carbon atoms can be used as the alkyl constituting the nonionic surfactant of component (B). In this alkyl an arbitrary —CH2— moiety may be replaced with —CH=CH—, cycloalkylene, or cycloalkenylene. Both alkyls from natural oils and fats such as palm oil, beef tallow, rapeseed oil, rice bran oil, fish oil, and the like and synthetic alkyl can be used.

Component (B1) can be obtained by: adding an alkylene oxide directly to a higher alcohol, higher fatty acid, or alkyl amine, etc.; reacting a higher fatty acid and the like with a polyethylene glycol obtained by adding an alkylene oxide to a glycol; or adding an alkylene oxide to an esterified product obtained by reacting a higher fatty acid with a polyhydric alcohol.

Examples of the alkylene oxide constituting component (B1) include ethylene oxide, propylene oxide, butylene oxide, and a random or block adduct of ethylene oxide/propylene oxide, and among these ethylene oxide, and a random or block adduct of ethylene oxide/propylene oxide are preferred. The number of moles to be added is preferably 5 to 50 moles, and preferably 50 to 100 wt % of the alkylene oxide to be added will be ethylene oxide. Hereinafter, ethylene oxide is sometimes abbreviated as EO, and when n moles thereof is added, it is expressed as EO(n).

Examples of component (B1) include polyoxyalkylene alkyl ether {component (B1-1)}; polyoxyalkylene higher fatty acid ester {component (B1-2)}; polyoxyalkylene polyhydric alcohol higher fatty acid ester {component (B1-3)}; polyoxyalkylene alkylphenyl ether {component (B1-4)}; polyoxyalkylene alkyl amino ether {component (B1-5)}; polyoxyalkylene alkyl alkanol amide {component (B1-6)}; and the like.

As the higher fatty acid constituting component (B1-2), component (B1-3), component (B1-6) and component (B2), a higher fatty acid from natural fatty acids such as palm oil, beef tallow, rapeseed oil, rice bran oil, fish oil, and the like can generally be used, but a chemically synthesized higher fatty acid may also be used.

Examples of the polyhydric alcohol constituting component (B1-3) and component (B2) include an alcohol with a hydricity of 3 to 8 such as glycerin, trimethylol-propane, pentaerythritol, sorbitan, sorbitol, sucrose, and the like. Glycerin, pentaerythritol, sorbitan, and sorbitol are especially preferred.

Examples of the alkylphenyl group constituting component (B1-4) include a monoalkylphenyl or dialkylphenyl having an alkyl group or groups of 8 to 12 carbon atoms.

Examples of the alkylamino constituting component (B1-5) include a monoalkylamino or dialkylamino having an alkyl group or groups of 8 to 24 carbon atoms. In these alkyl groups an arbitrary —CH$_2$— moiety may be replaced with —CH=CH—, cycloalkylene, or cycloalkenylene.

The alkyl alkanol amide constituting component (B1-6) is a group obtained by a dehydration reaction between an alkanol amine and a higher fatty acid. Examples of the alkanol amine include monoethanol amine, diethanol amine, monoisopropanol amine, and the like.

Among the various nonionic surfactants listed above for component (B), components (B1-1) to (B1-3); component (B1-6); and a polyhydric alcohol type nonionic surfactant such as glycerin, pentaerythritol, sorbitan, sorbitol, and the like are preferred.

One type thereof may be used alone, or 2 or more types may be used in combination as component (B).

Component (C), the anionic surfactant used in the present invention, may be any one of a carboxylic acid salt, sulfonic acid salt, sulfuric acid ester salt, or phosphoric acid ester salt. More specifically, a soap such as potassium oleate, sodium laurate, and the like can be used as the carboxylic acid salt. Furthermore, an alkyl sulfonate such as sodium lauryl sulfonate, sodium cetyl sulfonate; and an alkyl benzene sulfonate such as a lauryl benzene sulfonate, and the like can be used as the sulfonic acid salt. Alkyl sulfuric acid ester salts such as sodium stearyl sulfate and the like; and a sulfuric acid alkyl (polyoxyalkylene) ester salt such as a sodium sulfate wherein an oxyalkylene has been added to lauryl alcohol and the like can be used as the sulfuric ester salt. A phosphoric ester salt compound wherein a polyoxyalkylene has been added to a higher alcohol such as stearyl alcohol and the like can be used as the phosphoric acid ester salt. Among these alternatives, alkaline metal salts of sulfuric acid ester and alkaline metal salts of phosphoric acid esters wherein a higher alcohol and polyoxyalkylene have been added are preferred because of their excellent antistatic properties, and an alkaline metal salt of a phosphoric acid ester is especially preferred because it imparts smoothness to the fibers.

One type thereof may be used alone, or 2 or more types may be used in combination as component (C).

In the present invention both component (B) and component (C), or only one thereof can be used as an ingredient of the fiber treatment agent.

In the fiber treatment agent used in the present invention the weight ratio of the aforementioned component (A) to component (B) and/or component (C) is 20/80 to 80/20, preferably 25/75 to 75/25, and more preferably 30/70 to 70/30. When the weight ratio of component (A) to component (B) and/or component (C) lies within the range of 20/80 to 80/20, the antibacterial and deodorant properties are sufficient, and stability is also excellent. In this description, the amount of component (A) (plant extract) is expressed based on the remainder after extraction solvent evaporation, i.e., the amount of purities contained therein.

Additionally, the amount of the fiber treatment agent attached to the fibers is 0.2 to 5 wt %, preferably 0.2 to 3 wt %, and more preferably 0.3 to 1.5 wt % based on the total weight of the fiber. If the amount of fiber treatment agent lies within the range of 0.2 to 5 wt %, both deodorant and antistatic properties can be realized thereby. Moreover, preferably the amount of component (A) attached thereto will be at least 0.1 wt % based on the total weight of the fiber to enable deodorant properties to be sufficiently realized.

The range of the amount of fiber treatment agent attached to the fibers is generally the range required for maintaining workability during the fiber spreading step, and the effect of the invention is by no means adversely affected during fabrication of the fiber formed article subsequent to that step even if an amount beyond that range is attached thereto. When attaching the fiber treatment agent to the fibers it is preferable to dilute the fiber treatment agent in water and use it as a finishing agent to facilitate that process step.

Component (B) and component (C) may be used either alone or together in the fiber treatment agent used in the present invention. By using the two components together and setting the weight ratio of component (B) to component (C) preferably at 40/60 to 90/10, more preferably at 45/55 to 90/10, an excellent balance in the prevention of discoloration and antistatic properties can be realized, which is preferred because that is linked to enhanced workability in the fiber spreading step.

A cationic antibacterial agent such as an alkyl dimethyl benzyl ammonium salt such as benzalkonium chloride and the like; alkyl pyridinium salt such as cetylpyridinium chloride and the like; quaternary ammonium salt such as a dialkyl dimethyl ammonium salt and the like; and polylysine and the like can be added to the fiber treatment agent used in the present invention within a range that does not interfere with the effect of the present invention.

As needed, a pH regulator such as an alkanol amine of 2 to 4 carbon atoms; a chelating agent such as EDTA, sodium polyphosphoric acid, and the like; a skin protective agent such as squalane, sodium hyaluronic acid and the like; a water repellent such as dimethyl polysiloxane (silicone oil), a compound containing a perfluoroalkyl group, and the like; a fragrance such as phenylethyl alcohol, hexyl cinnamic aldehyde, and the like; a preservative; a rust inhibitor; a defoaming agent, and the like may also be added to the fiber treatment agent.

It is desirable that zinc oxide or the zinc oxide series complex oxide represented by General Formula (1) below be added to the fibers for the purpose of enhancing the antibacterial and deodorant properties and imparting durability to the plant extract in the antibacterial and deodorant fiber of the present invention:

$$M^{2+}_{(1-x)} M^{3+}_{x-\delta} O \quad (1)$$

(wherein $M^{2+}$ represents zinc or a divalent metal having zinc as an essential component thereof; $M^{3+}$ represents a trivalent metal selected from Al, Fe, and Ce, and preferably Al; x represents a number in the range $0<x\leq0.5$; and $\delta$ represents a cation lattice defect).

This zinc oxide series complex oxide refers to a solid solution having the same crystalline structure as ZnO wherein Al or another $M^{3+}$ has been substituted in ZnO and dissolved, or a mixture of that solid solution and a spinel ($M^{2+}M^{3+}_2O_4$), and the same exhibits almost the same diffraction pattern as ZnO in powder X-ray diffraction analysis.

In Formula (1), if the value of x is 0.5 or less, $Al_2O_3$, $Fe_2O_3$, $Ce_2O_3$ and the like are excluded from the solid solution of Formula (1), but even if these compounds are contained therein, the amount thereof will not be problematic, and the properties of the solid solution of Formula (1) will be sufficiently realized. Furthermore, if the value of x is at least within the range wherein $M^{2+}$ is activated, sufficient deodorant performance can be obtained. As a result, the range for the value of x in the complex oxide used in the present invention is $0<x\leq0.5$, preferably $0.1\leq x\leq0.4$, and more preferably $0.2\leq x\leq0.4$. The complex oxide can be obtained, for example, as the "PAZET SERIES" manufactured by Hakusuitech Ltd. or "SEABIO" manufactured by Sea Water Chemical Institute, Inc. Even if $Al_2O_3$, $Fe_2O_3$, $Ce_2O_3$ and the like, which are byproducts of the manufacturing process of the complex zinc oxide, are present in the complex oxide of Formula (1), the complex zinc oxide can be used as an antibacterial agent and deodorant provided the effect of the present invention is not lost as a result thereof. Moreover, $M^{2+}$ is zinc or a divalent metal having zinc as an essential component thereof and more specifically, by using metals other than zinc such as Ca, Mg, Cu, and the like in combination therewith, an effect is obtained such as a higher growth inhibitory effect not only toward bacteria such as *Escherichia coli*, *Staphylococcus aureus*, and the like but also toward molds such as black mold and the like.

Examples of methods for verifying qualitatively and quantitatively the content of the complex oxide of the present invention and the mix ratio of $M^{2+}$ and $M^{3+}$ therein include methods wherein surface analysis is performed by x-ray fluorescence or photoelectron spectroscopy of fine particles of the complex oxides exposed on the surface of the fibers; methods involving dissolution using a solvent capable of dissolving the thermoplastic resin constituting the fibers, filtering the complex oxide contained in the solution, separating the same by a means such as centrifugal separation and the like, and then performing elemental analysis by a means such as the surface analysis noted above and atomic absorption spectroscopy, ICP (high frequency inductively coupled plasma) emission spectroscopy, and the like. Naturally, the present invention is not limited to these exemplary methods, and verification can be performed by other means. Furthermore, combining these means is preferred because it facilitates determining whether the inorganics contained therein are a divalent and/or trivalent metal solid solution, and whether it is a product having a different metal oxide intermixed therein.

A suitable content for the metal oxide and zinc oxide series complex oxide used in the present invention is 0.1 to 10 wt %, preferably, 0.3 to 5 wt %, and more preferably 0.5 to 5 wt % with respect to the total weight of the fiber. When the content lies in the range of 0.1 to 10 wt %, it is not only possible to realize sufficient deodorant properties, but spinnability deterioration and loss from the surface of the fiber during nonwoven fabric fabrication will not occur; thus, good productivity can be maintained.

When the antibacterial and deodorant fiber of the present invention is a fiber comprising one type of thermoplastic resin component (monocomponent fiber), examples of the thermoplastic resin component used therein include a polyolefin resin, polyester resin, polyamide resin, tactic polystyrene resin, or a mixture thereof, and the like, but the fiber of the present invention is by no means limited thereto. Moreover, the fiber constituting the present invention can also be one obtained from a resin composition having an elastomer resin as the primary component thereof. Here, the term primary component means the component with the greatest content therein. An elastomer resin is a polymer material that has the properties of an elastic body similar to vulcanized rubber at normal temperatures (20 to 30° C.) (due to the soft segments of the molecule), and that can be processed at high temperatures using a conventional fiber forming machine without adaptation in the same manner as a conventional thermoplastic resin at (due to the hard segments in the molecule). Examples of such an elastomer resin include polystyrene elastomers, polyolefin elastomers, polyester elastomers, polyamide elastomers, and polyurethane elastomers. When such an elastomer resin is used, an elastic function can also be provided in addition to the original antibacterial and deodorant functions.

When the antibacterial and deodorant fiber of the present invention is a conjugate fiber, it constitutes at least 2 component thermoplastic resins. The thermoplastic resin referred to in the present invention is not particularly limited thereby provided it has fiber forming properties and can be melt-spun using a conventional melt-spinning apparatus. Polyolefin resins, polyester resins, polyamide resins, and thermoplastic elastomer resins, tactic polystyrene resins or a mixture thereof can be listed as examples thereof, and for the reasons noted below, use of a polyolefin resin as a sheath member is especially preferred.

The following can be used as the aforementioned polyolefin resin: high density polyethylene, linear low density polyethylene, low density polyethylene, polypropylene (propylene homopolymer), ethylene-propylene copolymer having propylene as the main component thereof, ethylene-propylene-butene-1 copolymer having propylene as the main component thereof, polybutene-1, polyhexene-1, polyoctene-1, poly 4-methyl pentene-1, polymethyl pentene, 1,2-polybutadiene, and 1,4-polybutadiene. Furthermore, a small amount of $\alpha$-olefin such as ethylene, butene-1, hexene-1, octene-1 or 4-methyl pentene-1 and the like may be included in these homopolymers as a copolymer component in addition to the monomer constituting the homopolymer. Moreover, a small amount of another ethylenically unsaturated monomer such as butadiene, isoprene, 1,3-pentadiene, styrene, $\alpha$-methyl styrene and the like may be included as a copolymer component. Additionally, 2 or more types of the aforementioned polyolefin resins may be mixed together and used. Not only polyolefin resins polymerized by a conventional Ziegler-Natta catalyst, but also polyolefin resins polymerized by a metallocene catalyst and copolymers thereof can be preferably used therein. Finally, the melt flow rate (hereinafter, MFR) of a polyolefin resin that can be most suitably used is not particularly limited in the present invention provided it lies within the spinnable range, but an MFR of 1 to 100 g/10 min is preferred, and 5 to 70 g/10 min is more preferred.

The present invention does not limit the properties of the polyolefin resin other than the aforementioned MFR, e.g., the Q value (weight average molecular weight/number average molecular weight), Rockwell hardness, number of branching methyl chains, and the like provided the requirements of the present invention are satisfied thereby.

The polyester resin can be obtained by condensation polymerization from a diol and a dicarboxylic acid. Examples of the dicarboxylic acid used in condensation polymerization of the polyester resin include terephthalic acid, isophthalic acid, 2,6-naphthalene dicarboxylic acid, adipic acid, sebacic acid, and the like. Examples of the diol to be used include ethylene glycol, diethylene glycol, 1,3-propanediol, 1,4-butanediol, neopentyl glycol, 1,4-cyclohexane dimethanol and the like. Polyethylene terephthalate can be preferably utilized as the polyester resin in the present invention. In addition, the polyester resin may be either a homopolymer or a copolymer polyester (co-polyester). As the copolymer components in such a case, a dicarboxylic acid component such as adipic acid, sebacic acid, phthalic acid, isophthalic acid, 2,6-naphthalene dicarboxylic acid and the like, and a diol component such as diethylene glycol, neopentyl glycol, and the like can be utilized. Furthermore, polylactate can also be preferably used therefor.

Nylon-4, nylon-6, nylon-46, nylon-66, nylon-610, nylon-11, nylon-12, poly(m-xylene adipamide) (MXD-6), polyparaxylylene decanamide (PXD-12), and poly (bis cyclohexyl methane decanamide) (PCM-12) can be used as the polyamide resin. Furthermore, an amide copolymer having a monomer used in the above polyamide resins as a structural unit thereof can also be used.

In the case of tactic polystyrene resins, the ratio of multiple repeating structural units is expressed, for example, by the term diad for 2 repeating units, triad for 3 repeating units, pentad for 5 repeating units, etc., as tacticity measured by $^{13}C$—NMR. Examples of the tactic polystyrene resins used in the present invention include polystyrene having syndiotacticity in the pentad fraction of normally not less than 85% or preferably not less than 95%, poly-alkyl styrenes such as polymethyl styrene, polyethyl styrene, polyisopropyl styrene, and the like; poly-halogenated styrenes such as polychloro styrene, polybromo styrene, polyfluorostyrene and the like; poly-halogenated alkyl styrenes such as polychloromethyl styrene and the like; poly alkoxy styrenes such as polymethoxy styrene, polyethoxy styrene, and the like; and polybenzoic acid styrene and the like. Naturally, these can be used alone or as mixtures thereof, and a copolymer having monomers mutually constituting these copolymers or a copolymer having these monomers as a primary component thereof can also be used.

In other words, these are copolymers having a syndiotactic styrene structure with 1 or more types of monomers selected from the aforementioned monomer groups and an olefin series monomer such as ethylene, propylene, butene, hexene, heptene, octene, decene, and the like; a diene series monomer such as butadiene, isoprene, and the like; a cyclic olefin monomer; cyclic diene monomer; or polar vinyl series monomer such as methyl methacrylate, maleic anhydride, acrylonitrile, and the like. Commercially available products can be used or these homopolymers or copolymers.

Among the aforementioned thermoplastic resins, polyolefin resins in particular have a low melting point and are easy to bond by heating, and they have a relatively high level of gas permeability. By adding fiber treatment agent to the polyolefin resin, for example, attaching or incorporating the fiber treatment agent to the polyolefin resin so as to add the fiber treatment agent to the fiber surface layer, response to odorants and inhibition of bacterial growth can proceed efficiently. In other words, the use of a polyolefin resin is preferred for the aforementioned monocomponent fiber or the sheath member of conjugate fiber.

Additives such as an antioxidant, photostabilizing agent, UV absorbing agent, neutralizing agent, nucleating agent, epoxy stabilizer, lubricant, antibacterial agent, flame retardant, antistatic agent, pigment, plasticizer, and the like may be added to the thermoplastic resin used in the present invention as needed within a range that does not hinder the effect of the present invention.

Thermal bonding capability can be realized by using a conjugate fiber comprising at least 2 types of thermoplastic resins as the antibacterial and deodorant fiber of the present invention. If the conjugate fiber comprises a core member and sheath member, for example, the thermoplastic resin of the sheath member will preferably have a lower melting point than the thermoplastic resin of the core member to impart sufficient thermal bonding capability to the conjugate fiber, and the sheath member will be exposed on the surface of the fiber. In the case of a thermoplastic single fiber, the primary fabricating method for making a fiber formed article involves coating the fibers with a binder and using a physical entangling method such as needle punch, spun lace, and the like. In these methods, the active ingredient may be covered over by the binder, or the active ingredient of the fiber treatment agent may be lost because of the needles, high-pressure water flow, and the like. Using a conjugate fiber, however, can minimize the loss of antibacterial and deodorant properties resulting from covering over and dropping off because a thermal bonding can be used for making a fiber formed article.

Not only a circular cross-sectional shape but also a variant cross-sectional shape (non-circular cross-sectional shape) can be used as the cross-sectional shape of the anti-bacterial and deodorant fiber of the present invention. Examples of a variant cross-sectional shape include, for example, star shape, elliptical shape, triangular shape, quadrangular shape, pentagonal shape, multilobe shape, array shape, T-shape, and horseshoe shape. In such cases the antibacterial and deodorant effect is enhanced because the surface area is increased. In addition to the above shapes, a hollow cross-section can also be used. In the case of conjugate fibers, examples of cross-sectional shapes include sheath-core, side-by-side, eccentric sheath-core, multilayer, radial, sea-island and other shapes, but the sheath-core, side-by-side, and eccentric sheath-core cross-sectional shapes are preferred because the complex oxides are easily and efficiently exposed, fabrication of the nonwoven fabric by thermal bonding is facilitated, and the like.

Examples of combinations of the thermoplastic resins constituting the antibacterial and deodorant conjugate fiber of the present invention expressed in the form of sheath member/core member are as follows: polyolefin resin/polyolefin resin; polyolefin resin/polyester resin; polyester resin/polyester resin; polyamide resin/polyester resin; and polyolefin resin/polyamide resin. Examples of the combination of polyolefin resin/polyolefin resin include the following: high density polyethylene/polypropylene; linear low density polyethylene/polypropylene; low density polyethylene/polypropylene; a binary or ternary copolymer of propylene and another α-olefin/polypropylene; linear low density polyethylene/high density polyethylene; and low density polyethylene/high density polyethylene.

Examples of a preferred combination of polyolefin resin/polyester resin include the following: polypropylene/polyethylene terephthalate; high density polyethylene/polyethylene terephthalate; linear low density polyethylene/polyethylene terephthalate; and low density polyethylene/polyethylene terephthalate. Instead of polyethylene terephthalate, polybutylene terephthalate, polytrimethylene terephthalate, and polylactate may also be used.

Examples of the combination of polyester resin/polyester resin include the following: copolymerized polyester/polyethylene terephthalate; polyethylene terephthalate/polybutylene terephthalate; polyethylene terephthalate/polytrimethylene terephthalate; and the like.

In the antibacterial and deodorant conjugate fiber of the present invention, the conjugate ratio of the sheath member to the core member is preferably in the range of 10/90 wt % to 90/10 wt %, and more preferably 30/70 wt % to 70/30 wt %. Both components will form a uniform cross-sectional shape when the conjugate ratio is established in this range. In the following explanation the unit for the conjugate ratio is percent by weight (wt %).

The present invention does not limit the method for attaching the fiber treatment agent to the fibers in the present invention, and the treatment agent may be attached to the fibers by contact with the oiling roll in the spinning and/or drawing process step, immersion in an immersion tank, spray atomization and the like. The treatment agent may be attached not only to the fibers themselves, but also to a web or fiber formed article. For example, during the nonwoven fabric fabrication step methods for attachment by direct contact with the web, immersion, or spraying can be utilized, and after the fibers are processed into a fiber formed article, attachment by direct contact, immersion, or spraying can be utilized. Additionally, a method wherein attachment is performed all at once using a mixture of the aforementioned components (A) to (C) is preferred, but a method wherein component (A), which is the deodorant component, and a surfactant containing component (B) and/or component (C) are attached separately in the spinning step, drawing step, or nonwoven fabric fabrication step. By protecting component (A) with component (B) and/or component (C), suppression of static electricity (antistatic effect) in the fiber spreading step during the nonwoven fabric fabrication step can be realized, and the loss of component (A) and discoloration caused by oxidation during long-term storage can be held to a minimum.

One example involves the following: after component (A) is attached to fibers manufactured by a well known method such as dry spinning, wet spinning, gel spinning, melt spinning and the like by means such as a touch roll and the like in the spinning step, a surfactant comprising component (B) and/or component (C) is attached on top of the layer of component (A) in the drawing step.

Another example involves the following: after component (A) is attached to a nonwoven fabric manufactured by a well known method such as web/water-jet processing, short fiber/air laid/thermal bond processing, melt blow spinning/thermal bond processing, spunbond spinning/thermal bond processing, and the like by means such as a touch roll, gravure roll and the like, a surfactant comprising component (B) and/or component (C) is attached on top of the layer of component (A). However, the present invention is by no means limited to these exemplary methods.

Examples of the fiber formed article using the antibacterial and deodorant fibers of the present invention include a net, web, knit, or nonwoven fabric and the like, and the use of the fibers in a nonwoven fabric is especially preferred. Well known methods such as the thermal bond method (through-air method, point bonding method), air laid method, needle punch method, water jet method and the like can be used as the method for producing the nonwoven fabric. After a web of short fibers is made with a carding machine and the like, the web can be made into a nonwoven fabric by the aforementioned methods for manufacturing a nonwoven fabric. A web can also be manufactured directly by the melt blow method or spunbond method, and then formed into a nonwoven fabric by the aforementioned methods therefor. In addition, fibers blended by a method such as cotton blend, spin blend, fiber blend, twisted union, twisted stitch, twisted fiber, and the like can be made into the form of a fabric by the aforementioned methods for manufacturing a nonwoven fabric. The fiber formed article obtained in the present invention may be used alone, or it may be used by laminating or integrating the same with a formed product such as another nonwoven fabric, knit fabric, mesh article, film, and the like.

The fiber product using the antibacterial and deodorant fibers of the present invention can be utilized in various ways in fiber products requiring hydrophilicity and water penetration properties, e.g., absorbent articles such as diapers, napkins, incontinence pads, etc.; medical hygiene supplies such as gowns, scrubs, etc.; interior furnishing materials such as wall coverings, Japanese translucent sliding window paper, floor coverings, etc.; daily living-related materials such as various covering cloths, garbage container coverings, etc.; toilet related products such as disposable toilets, toilet seat covers, etc.; pet products such as pet sheets, pet diapers, pet towels, etc.; general medical supplies; bedding materials; filter materials; nursing care products, and so forth.

The use of the antibacterial and deodorant fibers of the present invention or a nonwoven fabric using the same in an absorbent article is especially preferred because in addition to the deodorant properties thereof, it has the effect of protecting the skin from dermatitis such as diaper rash and the like. Diaper rash is thought to be caused by the production of ammonia due to direct contact of bacteria and enzymes present on the surface of the skin with excrement such as urine and the like, and this raises the pH of the skin, resulting in increased activity of proteolytic and lipolytic enzymes. However, the active ingredient of component (A) reacts with the ammonia that is produced and maintains a constant pH on the skin because it also has a weakly acidic buffering action, thereby protecting against diaper rash.

Furthermore, the added zinc oxide keeps the surface of the fibers in a state similar to a dry state, thereby imparting an overall feeling of smoothness to the touch. As a result, it plays an active role in skin care by its astringent, antiinflammatory, and antiallergy effects on the skin. This dry state not only has effects directly on the skin, but is also effective in mite control by inhibiting the growth of mites. The dry state exhibits this effect by disturbing the balance of moisture regulation in mites and suppressing their reproductive capability.

EXAMPLES

The present invention is described in detail below through examples, but is by no means limited thereto. The evaluations of properties in each example were performed by the methods shown below.

(Accelerated Test of Fiber Discoloration Resistance)

A sample of 100 g of test fiber was made into a carded web in a roller card testing machine at 25° C., and 65% relative humidity at a rate of 7 m/min, processed with a needle punch machine, and made into a needle punch nonwoven fabric with a mass per unit area of approximately 80 g/m². The fabric was cut into 8 cm×8 cm squares and immobilized on pasteboard. An exposure apparatus was prepared wherein the periphery of a kerosene heater was covered with metal so that the combustion gases of the kerosene stove would be captured therein. The nonwoven fabric sample was suspended 80 cm above the flame of the stove and exposed to the combustion gases for 3 hours while maintaining a temperature of approximately 100° C. inside the apparatus. Samples before and after exposure were visually compared, and scored for the presence or absence of discoloration such as yellowing, reddening, and the like using the following criteria.

Good (O): Almost no discoloration can be seen
Fair (Δ): Slight discoloration can be seen
Poor (x): Yellowing and reddening are conspicuous, and obvious discoloration can be seen (Amount of Fiber Treatment Agent Attached)

The amount of fiber treatment agent attached to the fibers was measured by rapid extraction using a rapid residual fat extraction apparatus model R-II (Tokai Keiki Co., Ltd.). A sample of 2 g of test fibers and fiber formed article (in the case of short fibers, if there was concern about spotting due to the method of attachment of the treatment agent, the sample was made into a carded web) was packed into a metal cylinder (16 mm ID, 130 mm long, base rounded like a mortar with a 1 mm hole at the lowest part), and 25 mL of methanol was divided into several portions and poured into the tube from the top. The liquid dripping from the hole in the bottom of the tube was captured in a heated aluminum saucer and the methanol was evaporated. The mass (g) of the residue in the aluminum saucer was then weighed and converted to the amount of treatment agent attached using the following formula.

Amount attached=(mass of residue/2)×100 (unit: %)

(Deodorant Properties Test)

The deodorant properties of the nonwoven fabrics obtained in the examples and comparative examples were assayed for ammonia and acetic acid in the following manner. A specified amount (3 g) of nonwoven fabric was placed into a Tedler bag (volume: 5 L) and sealed therein. Then using a syringe, air containing a specified concentration of odorant was injected into the Tedler bag so that that the total amount of gas would be 3 L. After a set amount of time had elapsed after injection of the gas, the gas in the Tedler bag was directly measured using gas detection tube (Model 81 for acetic acid, models 4LL and 4LT for hydrogen sulfide manufactured by Gastec Corporation), and the odorant removal rate was determined from the following formula.

Removal rate (%)=$\{(C_0-C)/C_0\} \times 100$ $C_0$: Initial concentration
C: Concentration of target odorant after 24 hours (Antibacterial Properties Test)

This test was performed in accordance with the standardized testing method of the Association of Antibacterial Treatments for Textiles, Japan (SEK). The entirety of a 0.4 g test sample dried in a clean bench after sterilization was inoculated uniformly with 0.2 mL of a liquid suspension of test bacteria that had been prepared to a viable bacterial count of $1 \times 10^5$ cells/mL in a 1/20 concentration of previously autoclaved nutrient broth and then cooled on ice. The sample was sealed with a sterile cap and incubated for 18 hours at 37±1° C., and the viable bacterial count after culturing was measured.

The samples were 2 types, which were a reference fabric (specified in the processing effectiveness evaluation test manual for antibacterial and deodorant processed products) and a processed fabric prepared from each example. The test bacteria were *staphylococcus aureus* bacteria (*Staphylococcus aureus* ATCC 6538P). The bacteriostatic activity value, which is the index of antibacterial properties, was calculated using the following formula.

Bacteriostatic activity value=log $B$-log $C$

Test validity condition of (log B-log A)>1.5 must be satisfied.
A: Mean bacterial cell count collected immediately after inoculation of reference fabric
B: Mean bacterial count collected after culturing reference fabric for 18 hours
C: Mean bacterial count collected after culturing processed fabric for 18 hours Items with a bacteriostatic activity value of 2.2 or higher are judged to be antibacterial.

(Plant Extract)

The following substances were used as the plant extract comprising component (A) of the fiber treatment agent.

Extract 1: L-17W (brand name, manufactured by Kankyo Kagaku Kaihatsu K.K.; extract of bamboo grass, Japanese buttebur, loofa, horsetail, and Japanese mugwort)

Extract 2: PANSHIRU (brand name, manufactured by Rilis Co., Ltd.; persimmon extract, persimmon polyphenols 5%)

Extract 3: TEAFURAN 30A (brand name, manufactured by Ito En, Ltd.; tea extract, tea polyphenols 40%)

(Fiber Treatment Agent and Addition Method Therefor)

Table 1 below shows the composition (units: wt %) of component (A), component (B), and component (C) constituting each fiber treatment agent.

TABLE 1

|     | Component | Fiber Treatment Agent | | | | | |
|-----|-----------|-----|-----|-----|-----|-----|-----|
|     |           | (1) | (2) | (3) | (4) | (5) | (6) |
| (A) | L-17W     | 40  | —   | 30  | 50  | —   | —   |
|     | PANSHIRU  | —   | 40  | —   | —   | 40  | —   |
|     | TEAFURAN 30A | — | —  | —   | —   | 60  | 55  |
| (B) | Sorbitan monooleate | 6 | 6 | — | — | — | — |
|     | Sorbitan monopalmitate | 16 | 16 | — | — | — | — |
|     | Stearic acid EO(5) | — | — | 14 | — | — | — |
|     | Stearic acid diethanolamide | — | — | 24 | 20 | — | — |
|     | Behenamide EO(10) | — | — | 22 | 10 | — | — |
|     | Hexaglycerol monostearate | — | — | — | 20 | — | — |

TABLE 1-continued

|  | | Fiber Treatment Agent | | | | | |
|---|---|---|---|---|---|---|---|
| Component | | (1) | (2) | (3) | (4) | (5) | (6) |
| (C) | (C8) Alkyl potassium phosphate | — | — | — | — | — | 27 |
|  | (C12) Alkyl potassium phosphate | 18 | 18 | 10 | — | — | 12 |
|  | (C18) Alkyl potassium phosphate | 20 | 20 | — | — | — | 6 |

As shown in Table 2, the fiber treatment agent was attached to the fiber in the spinning step and/or drawing step. The treatment agent comprising a mixture of component (A), component (B) and component (C) was attached in the spinning step.

(Metal Oxide and Addition Method Therefor)

The following substances were used as the metal oxide added to the thermoplastic resin.

Metal Oxide 1: ZnO

Metal Oxide 2: $Zn_{0.75}Al_{0.25}O$

A master batch of metal oxide powder was prepared and then added to the sheath member. The resin used for the master batch was the same resin as that used for the sheath member.

Table 2 shows the content of the metal oxide. The content thereof is also the content in the fibers.

(Thermoplastic Resin)

The following resins were used as the thermoplastic resin constituting the fibers.

Resin 1: High density polyethylene (abbreviated as PE), having a density of 0.96 g/cm$^3$, MFR (at 190° C. with load of 21.18 N) of 16 g/10 min, and melting point of 131° C.

Resin 2: Crystalline polypropylene (abbreviated as PP) having an MFR (at 230° C. with a load of 21.18 N) of 15 g/10 min, and melting point of 162° C.

Resin 3: Ethylene-proyplene-1-butene ternary copolymer (abbreviated as co-PP) with an ethylene content of 4.0 wt % and 1-butene content of 2.65 wt % having an MFR (at 230° C. with a load of 21.18 N) of 16 g/10 min, and melting point of 131° C.

Resin 4: Polyethylene terephthalate (abbreviated as PET) having an intrinsic viscosity of 0.65.

Resin 5: Polytrimethylene terephthalate (abbreviated as PPT) having an intrinsic viscosity of 0.92.

Table 2 shows the resins and combinations thereof used in the fibers.

(Melt Flow Rate (MFR) Measurement)

The melt flow rate was measured in accordance with JIS K 7210. The MI was measured in accordance with Condition D (test temperature of 190° C., load 2.16 kg) of Appendix A, Table 1, and the MFR was measured in accordance with Condition M (test temperature 230° C., load 2.16 kg).

(Nonwoven Fabric)

The following method and conditions were used as the method for producing the nonwoven fabric.

Through-Air Process (abbreviated as TA): Using the thermoplastic resins shown in Table 2, spinning was formed according to the content ratios (weight ratios) and cross-sectional shapes shown therein, and during that process the various fiber treatment agents shown in Table 1 were placed in contact with an oiling roll and attached to the fabric. After the drawing step, the fibers were dried to obtain fibers of 2.2 dtex. Next, the fibers were cut into short fibers with a cut length of 51 mm, and those were used as the test sample fibers.

The test sample fibers were made into a carded web in a roller carding machine, and the web was processed in a suction dryer and used as a nonwoven fabric with a mass per unit area of 25 g/m$^2$. Processing was conducted under the condition in which processing temperature was 130° C.

Examples 1 to 8, Comparitive Example 1

The performance of the conjugate fibers obtained as described above and the nonwoven fabrics prepared using the same were evaluated and measured based on the aforementioned evaluation methods. The results are shown in Tables 2-1 and 2-2.

TABLE 2-1

| | | | Example 1 | Example 2 | Example 3 | Example 4 |
|---|---|---|---|---|---|---|
| Fiber | Fiber treatment agent | Constituent | Agent (1) | Agent (2) | Agent (4) | Agent (1) |
| | | Amount attached (wt %) | 0.6 | 0.7 | 0.6 | 0.8 |
| | | Component (A) Component (B)/(C) | Spinning | Spinning | Spinning | Spinning |
| | Metal oxide | Substance | — | — | — | — |
| | | Content (wt %) | — | — | — | — |
| | Resin | Cross-sectional shape | Sheath-core | Sheath-core | Sheath-core | Eccentric core |
| | | Core | PP | PP | PET | PPT |
| | | Sheath | PE | PE | PE | PE |
| | | Sheath/core ratio (parts by weight) | 50/50 | 50/50 | 50/50 | 50/50 |
| Discoloration resistance | | | ○ | ○ | ○ | ○ |
| Antibacterial and deodorant tests | Acetic acid | 0 min | 50 ppm | 50 ppm | 50 ppm | 50 ppm |
| | | 15 min | 40 ppm | 25 ppm | 35 ppm | 38 ppm |
| | | 2 h | 35 ppm | 6 ppm | 25 ppm | 25 ppm |
| | | 24 h | 25 ppm | 0 ppm | 20 ppm | 18 ppm |
| | | Removal rate (%) | 50 | 100 | 60 | 64 |
| | Ammonia | 0 min | 60 ppm | 60 ppm | 60 ppm | 60 ppm |
| | | 15 min | 20 ppm | 55 ppm | 12 ppm | 15 ppm |
| | | 2 h | 1 ppm | 40 ppm | 0 ppm | 1 ppm |
| | | 24 h | 0 ppm | 30 ppm | 0 ppm | 0 ppm |
| | | Removal rate (%) | 100 | 50 | 100 | 100 |
| | Bacteriostatic activity value* | | 3.6 | 3.6 | 4 | 3.6 |

*Presence or absence of antibacterial properties

TABLE 2-2

|  |  |  | Example 5 | Example 6 | Example 7 | Example 8 | Comp Ex 1 |
|---|---|---|---|---|---|---|---|
| Fiber | Fiber treatment agent | Constituent | Agent (3) | Agent (4) | Agent (1) | Agent (6) | Agent (5) |
|  |  | Amount attached (wt %) | 0.5 | 0.6 | 0.4 | 0.5 | 0.6 |
|  |  | Component (A) | Spinning | Drawing | Spinning | Spinning | Spinning |
|  |  | Component (B)/(C) | Drawing | Spinning |  |  |  |
|  | Metal oxide | Substance | Oxide 1 | Oxide 2 | — | — | — |
|  |  | Content (wt %) | 1 | 1 | — | — | — |
|  | Resin | Cross-sectional shape | Sheath-core | Sheath-core | Sheath-core | Sheath-core | Sheath-core |
|  |  | Core | PP | PET | PP | PET | PP |
|  |  | Sheath | PE | PE | co-PP | PE | PE |
|  |  | Sheath/core ratio (parts by weight) | 50/50 | 50/50 | 40/60 | 50/50 | 50/50 |
| Discoloration resistance |  |  | ○ | ○ | ○ | Δ | X |
| Antibacterial and deodorant tests | Acetic acid | 0 min | 50 ppm | 50 ppm | 50 ppm | 50 ppm | 50 ppm |
|  |  | 15 min | 15 ppm | 12 ppm | 42 ppm | 25 ppm | 15 ppm |
|  |  | 2 h | 2 ppm | 1 ppm | 38 ppm | 12 ppm | 8 ppm |
|  |  | 24 h | 0 ppm | 0 ppm | 30 ppm | 3 ppm | 0 ppm |
|  |  | Removal rate (%) | 100 | 100 | 40 | 94 | 100 |
|  | Ammonia | 0 min | 60 ppm | 60 ppm | 60 ppm | 60 ppm | 60 ppm |
|  |  | 15 min | 25 ppm | 18 ppm | 26 ppm | 22 ppm | 12 ppm |
|  |  | 2 h | 10 ppm | 1 ppm | 15 ppm | 10 ppm | 1 ppm |
|  |  | 24 h | 2 ppm | 0 ppm | 4 ppm | 6 ppm | 0 ppm |
|  |  | Removal rate (%) | 96 | 100 | 93 | 90 | 100 |
|  | Bacteriostatic activity value* |  | 4.4 | 4.4 | 3.2 | 2.8 | 3.6 |

*Presence or absence of antibacterial properties

As the results in the above tables show, the fibers of the present invention exhibit bacterial growth inhibition and deodorant properties, and discoloration thereof is also controlled. From the standpoint of inhibiting fabric discoloration, the ratio of polyphenols in the fiber treatment agent is preferably in the range of 1 to 20 wt %.

A variety of fiber formed articles and fiber products requiring antibacterial and deodorant performance e.g., absorbent articles such as diapers, napkins, incontinence pads, etc.; medical hygiene supplies such as gowns, scrubs, etc.; interior furnishing materials such as wall coverings, Japanese translucent sliding window paper, floor coverings, etc.; daily living-related materials such as various covering cloths, garbage container coverings, etc.; toilet related products such as disposable toilets, toilet seat covers, etc.; pet products such as pet sheets, pet diapers, pet towels, etc.; general medical supplies; bedding materials; filter materials; nursing care products, and so forth, can be manufactured from the antibacterial and deodorant fibers of the present invention.

The invention claimed is:

1. An antibacterial and deodorant fiber containing zinc oxide and/or complex oxide represented by General Formula (1) below in the range of 0.1 to 10 wt % with respect to the total weight of the fiber:

$$M^{2+}_{(1-x_1)}M^{3+}_{x_1-\delta}O \quad (1)$$

wherein $M^{2+}$ represents zinc or a divalent metal having zinc as an essential component thereof; $M^{3+}$ represents a trivalent metal selected from Al, Fe, and Ce; $x_1$ represents a number in the range $0<x_1<0.5$; and $\delta$ represents a cation lattice defect, said fiber characterized in that a fiber treatment agent comprising at least a component (A), and a component (B)and/or a component (C)described below is attached thereto at 0.2 to 5 wt % of the total weight of the fiber, the fiber treatment agent containing 20 to 80 wt % of the component (A), and 80 to 20 wt % of the component (B) and/or component (C):

(A) at least one plant extract, said plant being at least one selected from the group consisting of tea leaves, aloe, bamboo, bamboo grass, Japanese butterbur (*Petasites japonica*), loofa (*Luffa cylindrica*), horsetail (*Equisetum arvense*), Japanese mugwort (*Artemisia princeps*), geranium (*Geranium nepalense* var. thunbergii), persimmon, and grapefruit;

(B) at least one nonionic surfactant selected from the group consisting of an alkylene oxide adduct type nonionic surfactant and a polyhydric alcohol type nonionic surfactant;

(C) at least one anionic surfactant selected from the group consisting of a carboxylic acid salt, sulfonic acid salt, sulfuric acid ester salt, and phosphoric acid ester salt.

2. The antibacterial and deodorant fiber according to claim 1, characterized in that the polyphenols contained in the plant extract are 1 to 20 wt % with respect to the weight of the fiber treatment agent.

3. The antibacterial and deodorant fiber according to claim 1, characterized in that the attached amount of the component (A) is at least 0.1 wt % with respect to the total weight of the fiber.

4. The antibacterial and deodorant fiber according to claim 1, characterized in that the alkylene oxide adduct nonionic surfactant of the component (B) is selected from the group consisting of a polyoxyalkylene alkyl ether, a polyoxyalkylene alkyl phenol, a polyoxyalkylene higher fatty acid ester, a polyoxyalkylene polyhydric alcohol higher fatty acid ester, a polyoxyalkylene higher aliphatic amine, a polyoxyalkylene higher fatty acid amide, and a polyoxyalkylene alkyl alkanol amide.

5. The antibacterial and deodorant fiber according to claim 1, characterized in that the polyhydric alcohol nonionic surfactant of the component (B) is selected from the group consisting of a higher fatty acid ester of glycerin, pentaerythritol, sorbitan, or sorbitol; a sucrose fatty acid ester; and a higher fatty acid alkanol amide.

6. The antibacterial and deodorant fiber according to claim 1, characterized in that the fiber is a conjugate fiber containing at least two types of thermoplastic resin.

7. The antibacterial and deodorant fiber according to claim 6, which is a sheath-core type conjugate fiber, at least one type of the thermoplastic resin being a polyolefin resin, and the resin being located in the sheath member thereof.

8. The antibacterial and deodorant fiber according to claim 1, characterized in that the antibacterial and deodorant fiber is a conjugate fiber, and the above metal oxide is kneaded and mixed into the sheath member thereof.

9. A fiber formed article using the antibacterial and deodorant fiber according to claim 1.

10. A fiber product using the fiber formed article according to claim 9.

* * * * *